(12) United States Patent
Liu et al.

(10) Patent No.: US 6,306,656 B1
(45) Date of Patent: Oct. 23, 2001

(54) PLANT EMBRYO—AND ALEURONE—SPECIFIC PROMOTER

(75) Inventors: Jin-Hao Liu, Calgary; Kuo-Joan Cheng, Richmond, both of (CA); Tein-Chin Chen, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/417,286

(22) Filed: Oct. 13, 1999

(51) Int. Cl.$^7$ .......................... C12N 15/11; C07H 21/02; C07H 21/04; A01H 5/00
(52) U.S. Cl. .................. 435/419; 435/320.1; 435/410; 536/23.1; 536/23.6; 536/24.1
(58) Field of Search .................................. 435/320.1, 410, 435/419; 536/23.1, 23.6, 24.1

(56) References Cited

PUBLICATIONS

Jin–Hao Liu et al., Identification and Characterization of a Novel Barley Gene that is ABA–Inducible and Expressed Specifically in embryo and Aleurone, May 1999, Journal of Experimental Botany, vol. 50, No. 334, pp. 727–728.*

Hill, Robert D. et al., "Abscisic Acid Structure–Activity Relationships in Barley Aleurone Layers and Protoplasts," Plant Physiology, vol. 108, No. 2, pp. 573–579, 1995.

Liu, Jin–Hao et al., "Post–transcriptional regulation of bifunctional α–amylase/subtilisin inhibitor expression in barley embryos by abscisic acid," Plant Molecular Biology, vol. 29, No. 5, pp. 1087–1091, 1995.

Luo, Ma et al., "Characterization of a Gene Family Encoding Abscisic Acid—and Environmental Stress–inducible Proteins of Alfalfa," The Journal of Biological Chemistry, vol. 267, No. 22, pp. 15367–15374, 1992.

Shen, Qingxi et al., "Functional Dissection of an Abscisic Acid (ABA)—Inducible Gene Reveals Two Independent ABA–Responsive Complexes Each Containing a G–Box . . . ," The Plant Cell, vol. 7, No. 3, pp. 295–307, 1995.

Skriver, Karen et al., "Cis–acting DNA elements responsive to gibberellin and its antagonist abscisic acid," Proc. Natl. Acad. Sci. U.S.A. , vol. 88, No. 16, pp. 7266–7270, 1991.

* cited by examiner

*Primary Examiner*—Sean McGarry
(74) *Attorney, Agent, or Firm*—Fish & Richardson P.C.

(57) ABSTRACT

The invention relates to a new barley promoter sequence useful for expression of heterologous proteins in plant cells.

10 Claims, 1 Drawing Sheet

```
  1 cctcggccgtctgatcgactgaaagatcttatcttggagtttagtatgggtcgtcggcccttctcctcctcagtaggtg  80
 81 caaaccatacaacacgtcttaacctaataatcatgacttgagatctttatttaaacttactgcataaatagaatttaaaa 160
161 aatgttaaataagtaaaataacatcatatttagattatacacatcactatagattcaaattacattataaatagacattt 240
241 aaaaattaaataggtaagatacattagcgatccagtatccaagtcacgatgtgttttgacttttccacgaaagagatcgc 320
321 ttgagttggaagaagcggctacaggacacgttgtcgccgcggctaagcctccgtcctccacgtactcacccttcccgaaa 400
401 gctacggccaccatgcccaagctggagcgaaggtccttgctcatgaagcacacgacacgcgcccaaagtcgcagcttcg  480
481 tggcgacccggtcgacatgccaccgcccgacctataagaaccacacccgcctcgagctctccacctcaacatcatcagga 560
561 tcaaccgcctcacgctttcggttccaaatccaaccacctccaccatcacctccgtgctccccgtgccacgcttcccctgt 640
641 ccgtcccagagctccaccagctagcagcc ATG GAC GGC AAG GGC TAC ACC ACA CCG CCG ACC GCG  705
  1                               M   D   G   K   G   Y   T   T   P   P   T   A   12

706 CCT GCG CCA CAG GCC GAG GCA GGA GCG CCT CAC TTC TAT CCC CCG ACG GAG CAC GGC ACC  765
 13 P   A   P   Q   A   E   A   G   A   P   H   F   Y   P   P   T   E   H   G   T    32

766 GCG CCA CAG CCG GGA TCG CAG GTC TCC TAT CCC CCG ATG CCA AAG GCC ATG GAT GGC CAG  825
 33 A   P   Q   P   G   S   Q   V   S   Y   P   P   M   P   K   A   M   D   G   Q    52

826 GAC GCC GCC GCG CCA CAG CCG GGA GCG CCG CCG CAC CCG TCC TCC CCA CTC ACG CAG CAG  885
 53 D   A   A   A   P   Q   P   G   A   P   P   H   P   S   S   P   L   T   Q   Q    72

886 GCC ATG GAG CTG GAG GGC AAG TAC GCC GCC CCA CAG CCG GGC ACT GGA GCT ACG CCG TCC  945
 73 A   M   E   L   E   G   K   Y   A   A   P   Q   P   G   T   G   A   T   P   S    92

946 CCC CTG ACG CAG CAA GCC GTG GAC GGC AAG GAC GCC GCC CCG ACA CCG CCC GCC GAG TCG 1005
 93 P   L   T   Q   Q   A   V   D   G   K   D   A   A   P   T   P   P   A   E   S   112

1006 GCG CCG TGG GGT ACG ACC CAG ATG GGT CCG CCA GCG GCG CCG GGG GCG CAT CCC GAG AAC 1065
113  A   R   W   G   T   T   Q   M   G   P   P   A   A   P   G   A   H   P   E   N  132

1066 CAG CAG GCA GCG CAG TGG ACG GCC ACG CGC GGG GAC CAG GAG CTG CCG CCG TAC GTC ATC 1125
133  Q   Q   A   A   Q   W   T   A   T   R   G   D   Q   E   L   P   P   Y   V   I  152

1126 ATG GGG GCA CCG GAG CCG GCG CCG GCG GCG TCG GCG CGG CGG ACT GAC AAG GAG GCC AGG 1185
153  M   G   A   P   E   P   A   P   A   A   S   A   R   R   T   D   K   E   A   R  172

1186 GAC AGC CCC ATG GAG CAC ATC CTC GAC TTC TTC AAC ACC TGG AGC CGC AAG GCC GAG GAG 1245
173  D   S   P   M   E   H   I   L   D   F   F   N   T   W   S   R   K   A   E   E  192

1246 CTC TCC TCC AAC ATC TGG CTC AAC CTG AAG ACG GCG CCG TCC ATG TCG GAC GCG GCG ATG 1305
193  L   S   S   N   I   W   L   N   L   K   T   A   P   S   M   S   D   A   A   M  212

1306 GGG AAG CTG AGC CTG GGG GCG AAG GCG ATC ACG GGG GGC GGC TTC GAG AAG CTC TAC AAG 1365
213  G   K   L   S   L   G   A   K   A   I   T   G   G   G   F   E   K   L   Y   K  232

1366 CAG ACC TTC GGC TCC GGC CCC GAC GAG CAC GTG AAG AAG ACG TTC GCC TGC TAC CTC TCC 1425
233  Q   T   F   G   S   G   P   D   E   H   V   K   K   T   F   A   C   Y   L   S  252

1426 ACG GCC ACG GGC CCC GTC GCC GGC ACG CTC TAC CTC ACC AAC ACC AAC GTC GCC TTC TGC 1485
253  T   A   T   G   P   V   A   G   T   L   Y   L   T   N   T   N   V   A   F   C  272

1486 AGC GAC CGC CCG CTC TCC TTC GCC GCG CCG TCC GGC CAG ACC GCC TGG AGC TAC TAC AAG 1545
273  S   D   R   P   L   S   F   A   A   P   S   G   Q   T   A   W   S   Y   Y   K  292

1546 GTC ATG ATC CCG CTC GCC AAG CTC GCC GCC GTC GAG CCC GTC ACG GCC AAG GAG AGC CCG 1605
293  V   M   I   P   L   A   K   L   A   A   V   E   P   V   T   A   K   E   S   P  312

1606 CCC GAG AGG TAC ATC CAC ATC GTC GCA GCA CCG GCC TAC GAG TGA tcggctgattgccgccgtgt 1670
313  P   E   R   Y   I   H   I   V   A   A   P   A   Y   E   *                      327

1671 acaagtgtccgtggctctctgctttgattgccgtgtttgtgctctgcttttgcgcggatctgtttagtgagtgcttgt  1750
1751 gtagtggatgtccgtgtgattatgtattgttgtctatacgcttttgtcgaaatttaacgcgttcttcttaattccttca 1830
1831 aatattcttctccacctcttgtacggtatattttgtgttactcggagttgggcactgtatttgaattttgagcatgttttc 1910
1911 tag                                                                              1940
```

Fig. 1

PLANT EMBRYO— AND ALEURONE— SPECIFIC PROMOTER

BACKGROUND OF THE INVENTION

Supplementation of hydrolytic enzymes in farm animal feed can improve agricultural efficiency by decreasing the amount of fecal material, and therefore the waste removal cost and environmental hazard. However, the high cost of producing such enzymes precludes its low value-added use as a feed supplement. Since rice bran (including the rice embryo and aleurone) is a major component of many animal feeds, expression of hydrolytic enzymes in rice tissues may provide a cost-effective means of decreasing the environmental impact of animal farming.

SUMMARY OF THE INVENTION

The invention is based on the discovery of a new barley promoter (as part of the gene designated aba45) that can promote transcription in rice embryo cells. Thus, the promoter of the invention can be used to express hydrolytic enzymes in rice bran tissues.

Accordingly, the invention features an isolated nucleic acid comprising SEQ ID NO:1, a barley aba45 promoter sequence that can promote expression of a heterologous gene in rice cells. The full sequence of the aba45 gene of the barley *Hordeum vulgare* cv. Himalaya is shown in FIG. 1.

The invention also features an isolated nucleic acid having a sequence that hybridizes to SEQ ID NO:2 under stringent conditions or that is at least 70% (e.g., at least 80, 90, 95, or 99%) identical to SEQ ID NO:2, the sequence promoting transcription in a plant cell (i.e., is capable of promoting transcription in a plant cell when operably linked to an open reading frame). SEQ ID NO:2 is the portion of the promoter upstream of the cDNA start site (see FIG. 1 and the description thereof below). The plant cell can be a plant embryo cell (i.e., derived from a plant embryo) or a plant aleurone cell (i.e., derived from a plant aleurone).

The invention also includes any vectors or transformed cells which contain a nucleic acid of the invention. Vectors include nucleic acid vectors, such as expression plasmids, or viral vectors. Transformed cells include eukaryotic and prokaryotic cells.

By "hybridizes under stringent conditions" is meant specific and non-covalent binding to an immobilized reference nucleic acids in the presence of 0.2×SSC (1.75 g/l NaCl, 0.88 g/l Na$_3$citrate. 2H$_2$O; pH 7.0) and 0.1% (w/v) sodium dodecylsulfate at 68° C.

An isolated nucleic acid is one which is separated from other nucleic acid molecules which are present in the natural source of the nucleic acid. An isolated nucleic acid is free of sequences which naturally flank the nucleic acid (i.e., sequences flanking the 5' and 3' ends of the nucleic acid) in the genomic DNA of the organism from which the nucleic acid is derived.

Where a nucleic acid molecule is said to have a specific percent identity to a reference nucleic acid molecule, the percent identity is determined by the algorithm of Myers and Miller, CABIOS, 1989, which is embodied in the ALIGN program (version 2.0), or its equivalent, using a gap length penalty of 12 and a gap penalty of 4 where such parameters are required. All other parameters are set to their default positions. Access to ALIGN is readily available. See, e.g., http://www2.igh.cnrs.fr\, bin/align-guess.cgi on the Internet.

The promoter sequence of the invention can be introduced into a variety of plant expression vectors for expressing exogenous proteins in plant embryo or aleurone tissue. Such exogenous proteins include hydrolytic enzymes such as phytases, cellulases, xylanases, β-glucanases, amylases, lipases, proteases, or any other polypeptide that increases the commercial value of the plant as an animal feed component. More specifically, the new promoter sequence and an open reading frame to which it is operably linked can be integrated into a plant genome (e.g., a rice genome) to produce transgenic plants that express hydrolytic enzymes. Methods of delivering nucleic acids into a plant cell, whether for transient or stable expression, are well known in the art of plant biology.

Other features or advantages of the invention will be apparent from the following detailed description, the drawing, and also from the claims.

BRIEF DESCRIPTION OF THE DRAWINGS

FIG. 1 is a representation of the DNA sequence for the aba45 gene of the barley *Hordeum vulgare* cv. Himalaya. The promoter sequence from positions 1 to 649 is designated SEQ ID NO:1. The sequence from position 1 to, but not including, the transcription start site (vertical arrow; position 587) is designated SEQ ID NO:2. The complete aba45 nucleic acid sequence (positions 1 to 1913) is designated SEQ ID NO:3. The amino acid sequence is designated SEQ ID NO:4. Additional features of FIG. 1 are discussed below.

DETAILED DESCRIPTION OF THE INVENTION

The invention relates to a new plant promoter sequence isolated from a barley plant. The sequence promotes expression in plant embryo or aleurone tissues or cells. Without further elaboration, it is believed that one skilled in the art can, based on the above disclosure, the drawing, and the description below, utilize the present invention to its fullest extent. The following examples are to be construed as merely illustrative of how one skilled in the art can isolate and use aba45 promoters from biological sources, and are not limitative of the remainder of the disclosure in any way. Any publications cited in this disclosure are hereby incorporated by reference.

As part of an endeavor toward the understanding of the molecular mechanism underlying the abscisic acid (ABA) induction of gene expression during seed development and germination, putative ABA binding proteins were cloned by screening expression libraries using an anti-idiotypic antibody (AB2) for ABA. A new cDNA designated aba45 and its promoter were isolated as follows.

The anti-(+)ABA monoclonal antibody 15-I-C5 was purchased from IDETEK, Inc. Mice were immunized four times intraperitoneally with 100 μg 15-I-C5 in phosphate buffer saline. Some of the primed mice were then boosted twice subcutaneously with 100 μg 15-I-C5 emulsified in incomplete Freund's adjuvant. The crude serum was withdrawn, and the titer of the antibody against 15-I-C5, designated AB2, was determined by an enzyme-linked immunosorbent assay. The total IgG antibodies were purified using Protein A sepharose beads and analyzed by Western blotting.

A λgt22 A phage library was constructed using mRNA isolated from ABA-treated aleurone protoplasts. The cDNA molecules were cloned using the Superscript λXgt22 A cDNA construction kit (GIBCO/BRL). Aleurone layers were prepared from mature seeds of barley (*Hordeum vulgare* cv. Himalaya) and incubated with 100 μM ABA for 48 hours in the dark as described in Hill et al., Plant Physiol. 108:573–579, 1995.

Protoplasts were prepared from aleurone layers according to Jacobsen et al., Plant Molecular Biology 16:713–724, 1991.

The phage expression library was screened with the AB2 antibody using standard techniques. Positive clones were isolated and cloned into Bluescript SK (Stratagene) plasmids using NotI and SalI. One of the positive clones, designated aba45, was sequenced using a double-strand DNA cycle sequencing kit (GIBCO/BRL).

The Universal GenomeWalker™ Kit (ClonTech) was used to isolate the 5' genomic sequence upstream of the aba45 cDNA by digesting barley genomic DNA with each of five restriction enzymes provided in the kit. The GenomeWalker adaptor provided in the kit was ligated to each restriction digest to create five uncloned libraries. Two gene-specific primers, N1 (5'-GCGGTGTGGTGTAGCCCTTGC-3'; SEQ ID NO:5) and N2 (5'-TGGCACGGGGAGCACGGAGGT-3'; SEQ ID NO:6), were synthesized and used to generate a 587 bp product containing the promoter sequence.

Referring to FIG. 1, aba45 contains only one possible open reading frame starting with ATG, which is GC-rich (70.6%). The open reading frame encodes a predicted 34.3 kDa protein containing 326 amino acids. The aba45 nucleic acid and protein sequence show no significant homology with any known DNA or protein sequences.

Structural analysis of the aba45 5' genomic sequence revealed a TATA box (double-underlined) at about position −72, counting from the transcription start site. Several motifs related to ABA-responsive complexes are present upstream of TATA box. The two boxed sequences are putative ABA-responsive elements (ABREs), present at positions −206 and −238, relative to the transcription start site. The underlined sequence at about position −83 is homologous to the coupling element of many ABA responsive promoters. A putative gibberellin response element (dotted underline) is found at about position −29 from the transcription start site.

RNA blot hybridizations were used to study the aba45 expression level in the presence or absence of ABA and/or gibberellin. Total RNA was isolated from embryos sampled 21 days after anthesis, using the acid phenol procedure described in Liu et al., Plant Molecular Biology 29:1087–1091, 1995. The embryos were cultured for 24 hours in various concentrations of phytohormones before RNA isolation. aba45 RNA in the samples were isolated and electrophoresed in agarose gels, and the aba45 RNA level determined as described in Luo et al., J. Biol. Chem. 267:15367–15364, 1992. Fifty micrograms of total RNA were loaded per lane, transferred onto a blot, and hybridized with a labeled aba45 cDNA probe.

The 1 to 100 $\mu$M ABA incubations increased steady-state level of aba45 mRNA. When 1 to 10 AM gibberellic acid was added to the 100 AM ABA treatment, the induction of aba45 gene expression was partially reversed. The expression pattern of aba45 in response to ABA and gibberellin was consistent with the presence of various putative regulatory elements in its 5' genomic sequence, as discussed above.

To determine the abundance of aba45 RNA in various barley tissues, RNA was isolated from the root, stem, leaf, fruit, embryo, and aleurone of plants at 5, 10, 15, 20, or 30 days after anthesis. aba45 mRNA was not detectable in roots, stem, leaf, or young fruit at any time. The transcript was most abundant in embryos at 20 days after anthesis. The results show that aba45 is developmentally regulated and is expressed to different levels in different plant tissues.

To determine whether the aba45 promoter could drive expression of a heterologous protein in a heterologous cell, primers 5 A1 (5'-CCCAAGCTTCCTCGGCCGTCTGATC-3'; SEQ ID NO:7) and ARC-3 S1 (5'-CGGGATCCGGCTGCTAGCTGGTG-GAGCTCTGGGACGGACA GGGGAAGCGTGGCACGGGGAGCAC-3'; SEQ ID NO:8) were used to amplify the full promoter (SEQ ID NO:1; FIG. 1). Primers 5 A1 and ARC-3 S1 facilitated cloning of the promoter by introducing HindIII and BamHI sites (underlined primer sequence), respectively, into the PCR product. The PCR product was digested with HindIII and BamHI and used to replace the 0.8 kb HindIII to BamHI fragment encompassing the cauliflower mosaic virus 35 S promoter in pBI221 (ClonTech). The resulting plasmid, paba45-GUS, contained the aba45 promoter operably linked to a $\beta$-glucuronidase (GUS) reporter.

The paba45-GUS plasmid was introduced into rice cells using the biolistic procedure described in Abenes et al., Plant Cell Rep. 17:1–7, 1997. *Oryza sativa* caryopses at 15 days after anthesis were surface-sterilized using 75% ethanol. Embryos were isolated and soaked in 10 $\mu$M ABA for 30 minutes before bombardment. Twenty milliliters of sterile 1% agarose were poured into a 90 mm petri dish, allowed to solidify, and overlaid with a sterile filter paper disc (Whatmann No. 1, 70 cm). Embryos were laid side by side in random orientation at the center of the disc.

Bombardments were carried out using the PDS-100/Helium particle gun (BioRad, Hercules, Cailf.) under the following conditions: 1.6 mm gold particles as microcarrier, 900 psi rupture disc pressure, 3 cm target distance, 25 mm Hg chamber vacuum; 10 $\mu$l of gold/DNA macrocarrier, and 0.9 $\mu$g DNA mass per shot. After bombardment, the embryos were kept at 27° C in the dark for 48 hours.

The embryos were then transferred from the petri dish into a GUS stain containing 0.1 M sodium phosphate (pH 7.0), 0.5 mM $K_3Fe(CN)_6$, 0.5 mM $K_4Fe(CN)_6$, 1 mM 5-bromo-4 chloro-3-indolyl-$\beta$-D-glucuronide-cyclohexylamine salt, and 25% methanol. The embryos were kept at 37° C for 24–36 hours, then observed under a microscope and photographed. Specific regions of all embryos stained positive for GUS activity, thereby confirming that the aba45 promoter could drive expression of a heterologous gene in a non-barley plant.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. An isolated nucleic acid comprising SEQ ID NO:1 or 2.

2. A vector comprising the isolated nucleic acid of claim 1.

3. A transformed cell comprising the isolated nucleic acid of claim 1.

4. The transformed cell of claim 3, wherein the transformed cell is a rice cell.

5. An isolated nucleic acid comprising a sequence that hybridizes to SEQ ID NO:2 under stringent conditions, wherein the sequence promotes transcription in a plant cell.

6. The isolated nucleic acid of claim 5, wherein the plant cell is a plant embryo cell.

7. The isolated nucleic acid of claim 5, wherein the plant cell is a plant aleurone cell.

8. A vector comprising the isolated nucleic acid of claim 5.

9. A transformed cell comprising the isolated nucleic acid of claim 5.

10. The transformed cell of claim 9, wherein the transformed cell is a rice cell.

* * * * *

SEQUENCE LISTING

<160> NUMBER OF SEQ ID NOS: 8

<210> SEQ ID NO 1
<211> LENGTH: 649
<212> TYPE: DNA
<213> ORGANISM: Hordeum vulgare

<400> SEQUENCE: 1

| | | | | | |
|---|---|---|---|---|---|
| cctcggccgt | ctgatcgact | gaaagatctt | atcttggagt | ttagtatggg | tcgtcggccc | 60 |
| tttctcctcc | tcagtaggtg | caaaccatac | aacacgtctt | aacctaataa | tcatgacttg | 120 |
| agatctttat | ttaaacttac | tgcataaata | gaatttaaaa | aatgttaaat | aagtaaaata | 180 |
| acatcatatt | tagattatac | acatcactat | agattcaaat | tacattataa | atagacattt | 240 |
| aaaaattaaa | taggtaagat | acattagcga | tccagtatcc | aagtcacgat | gtgttttgac | 300 |
| ttttccacga | aagagatcgc | ttgagttgga | agaagcggct | acaggacacg | ttgtcgccgc | 360 |
| ggctaagcct | ccgtcctcca | cgtactcacc | cttcccgaaa | gctacggccc | accatgccca | 420 |
| agctggagcg | aaggtccttg | ctcatgaagc | acacgacacg | cgcccaaagt | cgcagcttcg | 480 |
| tggcgacccg | gtcgacatgc | caccgcccga | cctataagaa | ccacccgc | ctcgagctct | 540 |
| ccacctcaac | atcatcagga | tcaaccgcct | cacgctttcg | gttccaaatc | caaccacctc | 600 |
| caccatcacc | tccgtgctcc | ccgtgccacg | cttcccctgt | ccgtcccag | | 649 |

<210> SEQ ID NO 2
<211> LENGTH: 587
<212> TYPE: DNA
<213> ORGANISM: Hordeum vulgare

<400> SEQUENCE: 2

| | | | | | |
|---|---|---|---|---|---|
| cctcggccgt | ctgatcgact | gaaagatctt | atcttggagt | ttagtatggg | tcgtcggccc | 60 |
| tttctcctcc | tcagtaggtg | caaaccatac | aacacgtctt | aacctaataa | tcatgacttg | 120 |
| agatctttat | ttaaacttac | tgcataaata | gaatttaaaa | aatgttaaat | aagtaaaata | 180 |
| acatcatatt | tagattatac | acatcactat | agattcaaat | tacattataa | atagacattt | 240 |
| aaaaattaaa | taggtaagat | acattagcga | tccagtatcc | aagtcacgat | gtgttttgac | 300 |
| ttttccacga | aagagatcgc | ttgagttgga | agaagcggct | acaggacacg | ttgtcgccgc | 360 |
| ggctaagcct | ccgtcctcca | cgtactcacc | cttcccgaaa | gctacggccc | accatgccca | 420 |
| agctggagcg | aaggtccttg | ctcatgaagc | acacgacacg | cgcccaaagt | cgcagcttcg | 480 |
| tggcgacccg | gtcgacatgc | caccgcccga | cctataagaa | ccacccgc | ctcgagctct | 540 |
| ccacctcaac | atcatcagga | tcaaccgcct | cacgctttcg | gttccaa | | 587 |

<210> SEQ ID NO 3
<211> LENGTH: 1898
<212> TYPE: DNA
<213> ORGANISM: Hordeum vulgare
<220> FEATURE:
<221> NAME/KEY: CDS
<222> LOCATION: (670)...(1632)

<400> SEQUENCE: 3

| | | | | | |
|---|---|---|---|---|---|
| cctcggccgt | ctgatcgact | gaaagatctt | atcttggagt | ttagtatggg | tcgtcggccc | 60 |
| tttctcctcc | tcagtaggtg | caaaccatac | aacacgtctt | aacctaataa | tcatgacttg | 120 |
| agatctttat | ttaaacttac | tgcataaata | gaatttaaaa | aatgttaaat | aagtaaaata | 180 |

-continued

```
acatcatatt tagattatac acatcactat agattcaaat tacattataa atagacattt      240
aaaaattaaa taggtaagat acattagcga tccagtatcc aagtcacgat gtgttttgac      300
ttttccacga aagagatcgc ttgagttgga agaagcggct acaggacacg ttgtcgccgc      360
ggctaagcct ccgtcctcca cgtactcacc cttcccgaaa gctacggccc accatgccca      420
agctggagcg aaggtccttg ctcatgaagc acacgacacg cgcccaaagt cgcagcttcg      480
tggcgacccg gtcgacatgc accgcccga cctataagaa ccacccgc ctcgagctct        540 ccacctcaac atcatcagga tcaaccgcct cacgctttcg gttccaaatc caaccacctc     600
caccatcacc tccgtgctcc ccgtgccacg cttccctgt ccgtcccaga gctccaccag      660 ctagcagcc atg gac ggc aag ggc tac acc aca ccg ccg acc gcg cct gcg    711
          Met Asp Gly Lys Gly Tyr Thr Thr Pro Pro Thr Ala Pro Ala
            1               5                  10 cca cag gcc gag gca gga gcg cct cac ttc tat ccc ccg acg gag cac      759
Pro Gln Ala Glu Ala Gly Ala Pro His Phe Tyr Pro Pro Thr Glu His
 15                  20                  25                  30 ggc acc gcg cca cag ccg gga tcg cag gtc tcc tat ccc ccg atg cca      807
Gly Thr Ala Pro Gln Pro Gly Ser Gln Val Ser Tyr Pro Pro Met Pro
                 35                  40                  45 aag gcc atg gat ggc cag gac gcc gcc gcg cca cag ccg gga gcg ccg      855
Lys Ala Met Asp Gly Gln Asp Ala Ala Ala Pro Gln Pro Gly Ala Pro
             50                  55                  60 ccg cac ccg tcc tcc cca ctc acg cag gcc atg gag ctg gag ggc aag      903
Pro His Pro Ser Ser Pro Leu Thr Gln Ala Met Glu Leu Glu Gly Lys
         65                  70                  75 tac gcc gcc cca cag ccg ggc act gga gct acg ccg tcc ccc ctg acg      951
Tyr Ala Ala Pro Gln Pro Gly Thr Gly Ala Thr Pro Ser Pro Leu Thr
     80                  85                  90 cag caa gcc gtg gac ggc aag gac gcc gcc ccg aca ccg ccc gcc gag      999
Gln Gln Ala Val Asp Gly Lys Asp Ala Ala Pro Thr Pro Pro Ala Glu
 95                 100                 105                 110 gcg cgg tgg ggt acg agg cag atg ggt ccg cca gcg gcg ccg ggg gcg     1047
Ala Arg Trp Gly Thr Arg Gln Met Gly Pro Pro Ala Ala Pro Gly Ala
                115                 120                 125 cat ccc gag cag cag gca gcg cag tgg acg gcc acg cgc ggg gac cag     1095
His Pro Glu Gln Gln Ala Ala Gln Trp Thr Ala Thr Arg Gly Asp Gln
            130                 135                 140 gag ctg ccg ccg tac gtc atc atg ggg gca ccg gag ccg gcg ccg gcg     1143
Glu Leu Pro Pro Tyr Val Ile Met Gly Ala Pro Glu Pro Ala Pro Ala
        145                 150                 155 gcg tcg gcg cgg cgg act gac aag gag gcc agg gac agc ccc atg gag     1191
Ala Ser Ala Arg Arg Thr Asp Lys Glu Ala Arg Asp Ser Pro Met Glu
    160                 165                 170 cac atc ctc gac ttc ttc aac acc tgg agc cgc aag gcc gag ctc tcc     1239
His Ile Leu Asp Phe Phe Asn Thr Trp Ser Arg Lys Ala Glu Leu Ser
175                 180                 185                 190 tcc aac atc tgg ctc aac ctg aag acg gcg ccg tcc atg tcg gac gcg     1287
Ser Asn Ile Trp Leu Asn Leu Lys Thr Ala Pro Ser Met Ser Asp Ala
                195                 200                 205 gcg atg ggg aag ctg agc ctg ggg gcg aag gcg atc acg ggg ggc ggc     1335
Ala Met Gly Lys Leu Ser Leu Gly Ala Lys Ala Ile Thr Gly Gly Gly
            210                 215                 220 ttc gag aag ctc tac aag cag acc ttc ggc tcc ggc ccc gac gag cac     1383
Phe Glu Lys Leu Tyr Lys Gln Thr Phe Gly Ser Gly Pro Asp Glu His
        225                 230                 235 gtg aag aag acg ttc gcc tgc tac ctc acg gcc acg ggc ccc gtc gcc     1431
Val Lys Lys Thr Phe Ala Cys Tyr Leu Thr Ala Thr Gly Pro Val Ala
    240                 245                 250
```

-continued

```
ggc acg ctc tac ctc acc aac acc aac gtc gcc ttc tgc agc gac cgc    1479
Gly Thr Leu Tyr Leu Thr Asn Thr Asn Val Ala Phe Cys Ser Asp Arg
255                 260                 265                 270 ccg ctc tcc ttc gcc gcg ccg tcc ggc cag acc gcc tgg agc tac tac    1527
Pro Leu Ser Phe Ala Ala Pro Ser Gly Gln Thr Ala Trp Ser Tyr Tyr
            275                 280                 285 aag gtc atg atc ccg ctc gcc aag ctc gcc gcc gtc gag ccc gtc acg    1575
Lys Val Met Ile Pro Leu Ala Lys Leu Ala Ala Val Glu Pro Val Thr
        290                 295                 300 gcc aag gag agc ccg ccc gag agg tac atc cac atc gtc gca gca ccg    1623
Ala Lys Glu Ser Pro Pro Glu Arg Tyr Ile His Ile Val Ala Ala Pro
    305                 310                 315 gcc tac gag tgatcggctg attgccgccg tgtacaagtg tccgtggctc            1672
Ala Tyr Glu
    320 tctgcttttg attgccgtgt ttgtgctctg cttttttgcgc ggatctgttt agtgagtgct 1732 tgtgtagtgg atgtccgtgt gattatgtat tgttgtctat acgcttttgt cgaaatttaa  1792 cgcgttcttc ttaatttcct tcaaatattc ttctccacct cttgtacggt atatttgtgt  1852 tactcggagt tgggcactgt atttgaattt tgagcatgtt ttctag                 1898
```

<210> SEQ ID NO 4
<211> LENGTH: 321
<212> TYPE: PRT
<213> ORGANISM: Hordeum vulgare

<400> SEQUENCE: 4

```
Met Asp Gly Lys Gly Tyr Thr Thr Pro Pro Thr Ala Pro Ala Pro Gln
 1               5                  10                  15

Ala Glu Ala Gly Ala Pro His Phe Tyr Pro Pro Thr Glu His Gly Thr
            20                  25                  30

Ala Pro Gln Pro Gly Ser Gln Val Ser Tyr Pro Pro Met Pro Lys Ala
        35                  40                  45

Met Asp Gly Gln Asp Ala Ala Ala Pro Gln Pro Gly Ala Pro Pro His
    50                  55                  60

Pro Ser Ser Pro Leu Thr Gln Ala Met Glu Leu Glu Gly Lys Tyr Ala
65                  70                  75                  80

Ala Pro Gln Pro Gly Thr Gly Ala Thr Pro Ser Pro Leu Thr Gln Gln
                85                  90                  95

Ala Val Asp Gly Lys Asp Ala Ala Pro Thr Pro Pro Ala Glu Ala Arg
            100                 105                 110

Trp Gly Thr Arg Gln Met Gly Pro Pro Ala Ala Pro Gly Ala His Pro
        115                 120                 125

Glu Gln Gln Ala Ala Gln Trp Thr Ala Thr Arg Gly Asp Gln Glu Leu
    130                 135                 140

Pro Pro Tyr Val Ile Met Gly Ala Pro Glu Pro Ala Pro Ala Ala Ser
145                 150                 155                 160

Ala Arg Arg Thr Asp Lys Glu Ala Arg Asp Ser Pro Met Glu His Ile
                165                 170                 175

Leu Asp Phe Phe Asn Thr Trp Ser Arg Lys Ala Glu Leu Ser Ser Asn
            180                 185                 190

Ile Trp Leu Asn Leu Lys Thr Ala Pro Ser Met Ser Asp Ala Ala Met
        195                 200                 205

Gly Lys Leu Ser Leu Gly Ala Lys Ala Ile Thr Gly Gly Phe Glu
    210                 215                 220
```

```
Lys Leu Tyr Lys Gln Thr Phe Gly Ser Gly Pro Asp Glu His Val Lys
225                 230                 235                 240

Lys Thr Phe Ala Cys Tyr Leu Thr Ala Thr Gly Pro Val Ala Gly Thr
                245                 250                 255

Leu Tyr Leu Thr Asn Thr Asn Val Ala Phe Cys Ser Asp Arg Pro Leu
                260                 265                 270

Ser Phe Ala Ala Pro Ser Gly Gln Thr Ala Trp Ser Tyr Tyr Lys Val
            275                 280                 285

Met Ile Pro Leu Ala Lys Leu Ala Ala Val Glu Pro Val Thr Ala Lys
        290                 295                 300

Glu Ser Pro Pro Glu Arg Tyr Ile His Ile Val Ala Ala Pro Ala Tyr
305                 310                 315                 320

Glu

<210> SEQ ID NO 5
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 5
gcggtgtggt gtagcccttg c                                        21

<210> SEQ ID NO 6
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 6
tggcacgggg agcacggagg t                                        21

<210> SEQ ID NO 7
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 7
cccaagcttc ctcggccgtc tgatc                                    25

<210> SEQ ID NO 8
<211> LENGTH: 64
<212> TYPE: DNA
<213> ORGANISM: Artificial Sequence
<220> FEATURE:
<223> OTHER INFORMATION: Synthetically generated primer

<400> SEQUENCE: 8
cgggatccgg ctgctagctg gtggagctct gggacggaca ggggaagcgt ggcacgggga   60
gcac                                                           64
```